United States Patent [19]

Goof

[11] 4,205,236
[45] May 27, 1980

[54] FINGER OPERATED CONTROL SYSTEM FOR HAND-HELD APPLIANCES

[76] Inventor: Sven K. L. Goof, Gammel Strandvej 236 B, Humlebaek, Denmark, DK-3050

[21] Appl. No.: 823,422

[22] Filed: Aug. 10, 1977

Related U.S. Application Data

[62] Division of Ser. No. 667,831, Mar. 17, 1976.

[30] Foreign Application Priority Data

Mar. 20, 1975 [DK] Denmark .............................. 1184/75
Mar. 20, 1975 [DK] Denmark .............................. 1185/75

[51] Int. Cl.$^2$ ........................ H01H 35/24; A61C 3/02
[52] U.S. Cl. ................................ 307/118; 200/81 H; 433/99
[58] Field of Search ............... 336/30, 136; 200/81 H, 200/157, 5 E, DIG. 43; 310/34, 23; 32/27; 73/728, 729; 307/112, 118

[56] References Cited

U.S. PATENT DOCUMENTS

| | | | |
|---|---|---|---|
| 2,838,629 | 6/1958 | Panzenhagen | 200/81 H |
| 3,080,720 | 3/1963 | Downs et al. | 200/81 H |
| 3,437,964 | 4/1969 | Tausch | 336/30 |
| 3,545,125 | 12/1970 | Okuma | 200/81 H |
| 3,638,496 | 2/1972 | King | 73/728 |

FOREIGN PATENT DOCUMENTS 1296033  11/1972  United Kingdom .................. 200/81 H

*Primary Examiner*—L. T. Hix
*Assistant Examiner*—James L. Dwyer
*Attorney, Agent, or Firm*—Fleit & Jacobson

[57] ABSTRACT

An improved control system for hand-held appliances, in particular but not exclusively dental instruments is disclosed. The basic features of the improved control system are a closed or sealed enclosure or container to be mounted on a part of the appliance, preferably on the exterior surface of a handle portion thereof. The enclosure contains a deformable working medium body such as a fluid body which is adapted to effect actuation, operation or control of an actuatable device associated with the appliance. The actuatable device may be a regulator, a transducer or a motor. The control system is an indirectly acting type in which the working medium is displaced by locally compressing the enclosure. This displacement is used to move or operate a movable wall part of the enclosure which, in turn, operates a transducer or regulator unit in response to the degree of compression of the enclosure. The transducer or regulator unit is connected to an external circuit for changing specific characteristics or properties thereof.

11 Claims, 15 Drawing Figures

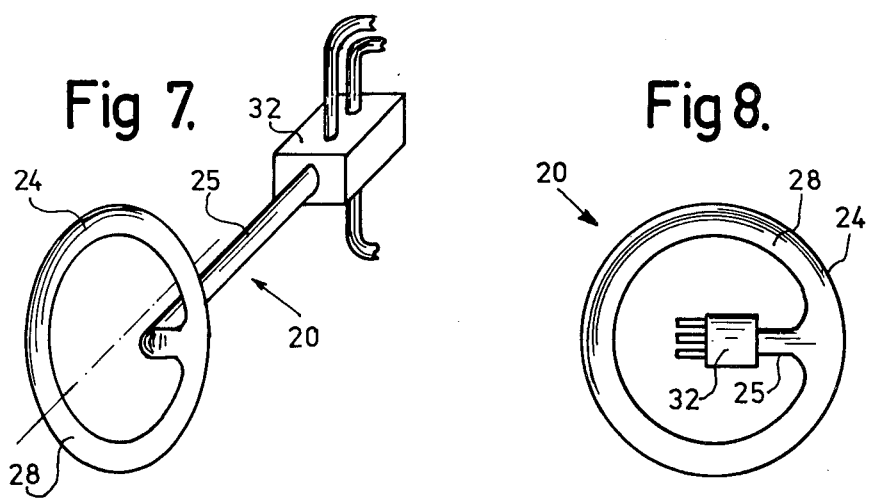
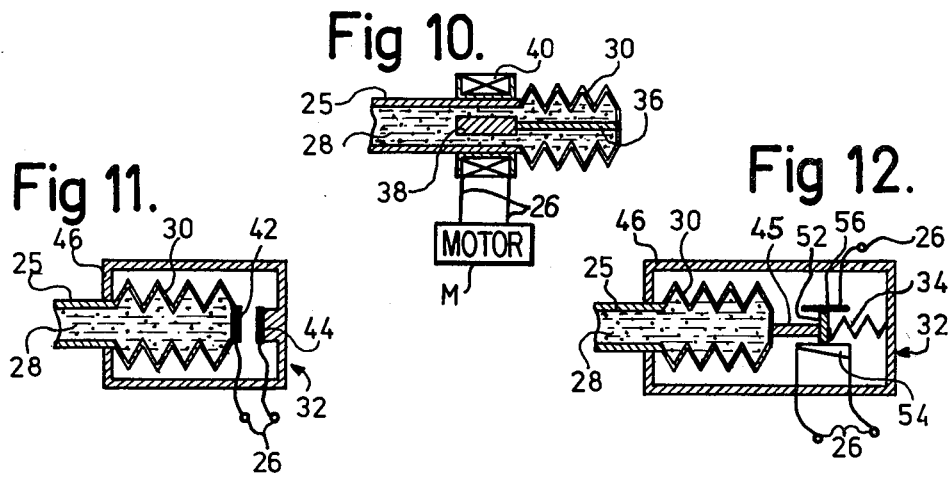
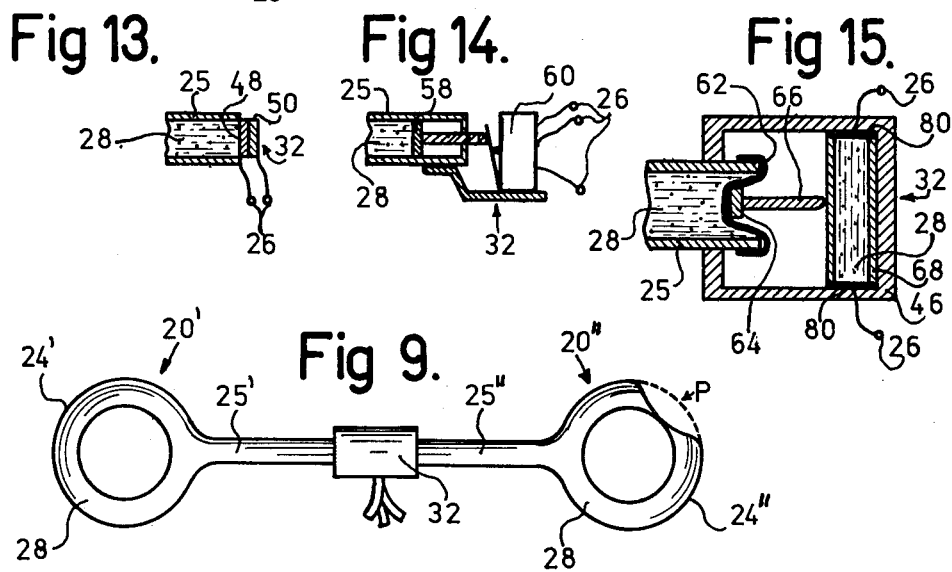

FINGER OPERATED CONTROL SYSTEM FOR HAND-HELD APPLIANCES

This is a divisional of application Ser. No. 667,831 filed Mar. 17, 1976.

The present invention relates to control systems in general and, more specifically, to a finger operated control system for hand-held appliances and for controlling an actuatable device associated with the appliance.

Hand-held appliances or instruments such as drills have been operated and controlled by means of finger operated means such as push buttons, tilting or toggle switches, and sliding switches in order to control one or more working conditions of the appliance, e.g., the rotational speed of a drill.

In connection with a number of types of hand-held appliances, such traditional control means are, however, not always suitable. This is, in particular, pronounced with dental instruments of different types in which it is decisive that the instruments are cleaned in an easy and effective manner after the treatment of each patient. Known control means of the types mentioned above are therefore not appropriate, since they have corners and the like in which bacteria would rather easily survive a disinfection.

Another fact which makes the traditional control means unsuited in connection with various types of hand-held appliances, and in particular in connection with dental instruments, is that an appliance having such control means must be taken and held in the hand in one particular and quite definite way. For instance, dental instruments are usually held in the same manner as a pencil, and the finger, usually the forefinger, used to operate and control the instrument must therefore be placed at the area of the operatable part of the control means of the instrument. Accordingly, if the control means is of the known type mentioned above, a dentist has to twist or turn his underarm and wrist considerably, e.g., when treating a patient's upper teeth, and this may cause very awkward and bad working positions.

Besides, the traditional control systems require rather much space which, in turn, limits the possibility of placing them in or on the appliance. For example, sliding resistances or other traditional control devices to be mounted in the interior of the appliance require certain dimensions. In connection with several types of appliances, in which small external dimensions are important, this often has the consequence that the control means must be located where space is available, which, in turn, may have the consequence either that the external operatable parts have to be situated at an inconvenient place or that unfavorable mechanical connecting links have to be used between the exterior operatable parts and the interior control devices of the control means.

Furthermore, the traditional control means are often vulnerable to impacts and blows.

On this background, it is an object of the present invention to provide a control system for hand-held appliances which may be located practically anywhere in or on such an appliance.

Another object of the present invention is to provide a control system having exposed outer surfaces of a simple shape well suited for cleaning when mounted on a hand-held appliance.

Still another object of the invention is to provide a control system being relatively resistant to impacts or blows.

Yet another object of the invention is to provide a hand held appliance having a control system being operable with one finger in any angular position of the appliance about a longitudinal axis thereof even when held and operated with one hand as a pencil.

These and several other objects and advantages are implemented by the control system according to the invention which is peculiar by comprising a sealed and compressible enclosure to be mounted on an appliance, and a deformable medium body enclosed in said enclosure, said medium body being adapted to cause control of an actuatable device associated with the appliance responsive to the degree of compression exerted on said enclosure.

The expression "actuatable device" as used herein is contemplated to cover such devices which may be actuated, operated or controlled such as transducers, valves or motors.

According to the invention, the working medium is displaced by compressing the enclosure member of the control device. This displacement is used to move or operate a movable wall part of the enclosure member which, in turn, operates a movable member of a control unit in response to the degree of compression of the enclosure. The control unit may then variable actuate the actuatable device responsive to the degree of compressing the enclosure member.

In the following, the present invention will be described in further details departing from specific embodiments and with reference to the drawings wherein:

FIGS. 5-9 are schematic illustrations of various compressible enclosure members and control units of control devices embodying the invention; and FIGS. 10-15 are sectional views schematically illustrating various types of control units for control devices according to the invention.

Figure 1:
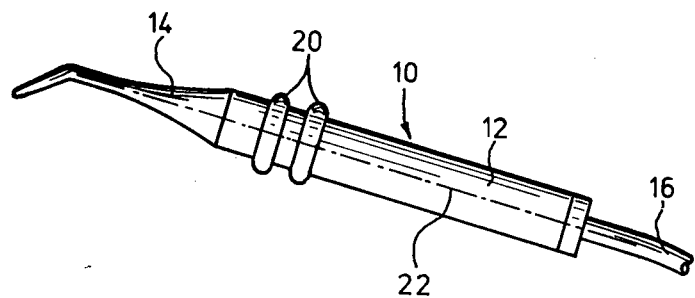
FIGS. 1-4 illustrate typical examples of hand-held appliances each provided with a control system according to the invention.

FIG. 1 shows a hand-held appliance 10 in the form of a dental syringe having a handle portion 12 and a nozzle member 14 with a supply tube 16 for supplying two fluids, the mixing ratio and flow rate thereof being controllable by means of respective finger operatable control systems according to the invention. Each control system or device comprises a compressible or collapsible enclosure member 20 and a working fluid 28 contained therein, said fluid being adapted to operate at least one valve in the syringe 10 by squeezing the enclosure 20 against the handle portion 12, dependent on the degree of compression. Each enclosure 20 is tubular and extends annularly around the handle portion 12 and has a branch portion which extends in the interior of the handle portion to a control unit for the valve or valves. The annular portion of the enclosure 20 of the control system is positioned coaxially relative to the longitudinal axis 22 of the handle portion 12. Each control device can be operated by squeezing anywhere on the annular portion of the enclosure so that the syringe 10 may be operated when in all angular positions about the axis 22, also when held as a pencil.

Figure 2:
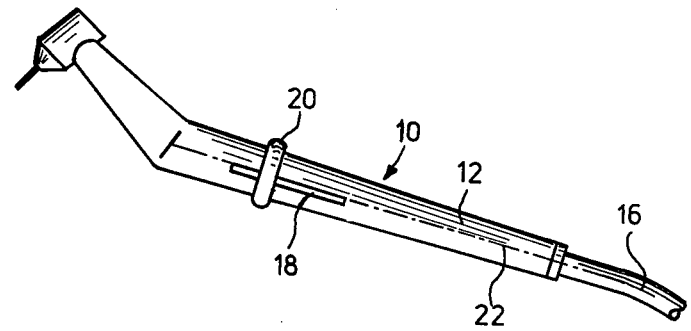

The hand-held appliance 10 shown in FIG. 2 is a drill, the rotational speed thereof being controlled by a control system according to the invention. The enclosure member 20 extends annularly around the exterior of the handle portion 12 and has a branch portion which extends to a motor control unit in the interior of the handle 12. This embodiment of the control system is adapted to be adjustable along the handle portion, the branch portion of the enclosure member extending into the interior of the handle portion 12 through a longitudinal slot 18. Thereby, the operator is able to move the control system into the most convenient position for the desired grip. The control unit in the interior of the handle portion 12 may be either stationarily or movably positioned.

Figure 3:
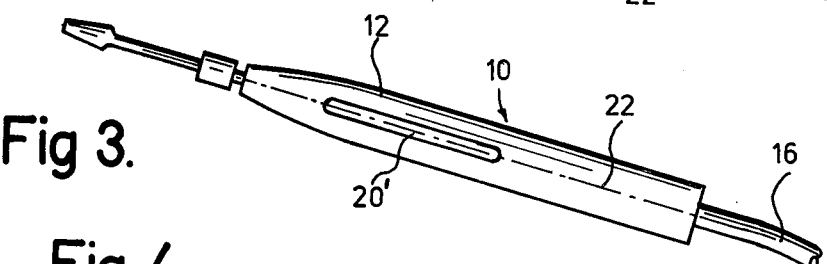
Figure 4:
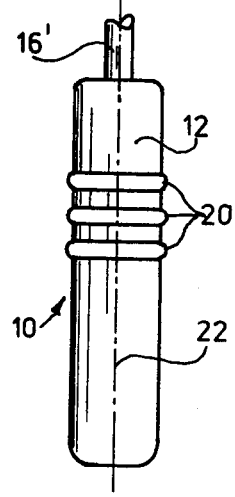

FIG. 3 shows a screw driver 10 provided with a finger-operatable control system according to the invention having an elongated tubular enclosure member 20' positioned along the handle portion 12, and having the control unit belonging thereto in the interior of the handle portion 12. This embodiment of the control system makes it possible to control the speed of revolutions at several locations along the handle portion 12, which facilitates the operation of the screw driver which is often suspended in the supply cable 16 ready for operation. Even though the enclosure 20 shown only extends along a part of the handle 12, it may be advantageous that the enclosure member extends along the entire length of the handle. FIG. 4 shows a remote control handle 10 of the type which may be suspended in a support cable 16. In the embodiment shown, three enclosure members 20 are provided around the handle portion 12, and each enclosure 20 may be operated anywhere around the periphery of the handle portion to operate associated control units in the interior of the handle portion. Control signals provided by the control units being transmitted through the support cable 16' to an actuatable device, such as a motor, associated therewith.

Figure 5:
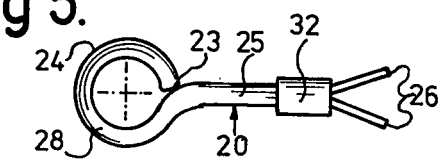

FIG. 5 shows a finger-operatable control system according to the invention having an enclosure member 20 of resilient plastic material, the annular portion 24 thereof being constituted by a part of a tube. One end of the tube is closed at 23, and the other end being connected to a control unit 32 through a connection branch 25. The unit 32 has two terminals 26 for connection with an electric circuit (not shown) and an actuatable device to be controlled. The enclosure member 20 is filled with a working fluid 28, either in the form of gas, liquid, paste or gel, and when the annular portion 24 is compressed, the working fluid is displaced to operate movable parts in the control unit 32, an electric circuit connected to terminals 26 may be changed as to capacitance, inductance, resistance or contact positions, depending on the type of actuatable device which is included in or associated with the circuit.

Figure 6:
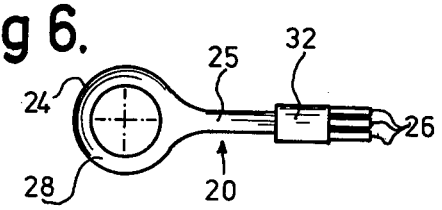

In FIG. 6 the annular portion 24 of the enclosure is shaped as a toroid and the connection branch 25 is an appendix thereto, which, as in FIG. 5, is connected to the control unit 32, here shown as having three terminals 26. The embodiments shown in FIGS. 5 and 6 are adapted for mounting around an elongate appliance, and the connection branch 25 may extend internally or externally along a handle portion thereof. In the latter case, the appliance may be controlled both along the periphery of the annular portion of the enclosure member and along the length of the connection branch 25.

FIG. 7 shows an embodiment in which the connection branch 25 extends from the annular portion 24 of the enclosure, at first radially inwardly, and then along the axis of the annular portion to the control unit 32. The control unit 32 incorporates an actuatable device shown schematically as a switching valve. The working fluid 28 in the enclosure member communicates operatively with a movable switching member of the valve. FIG. 8 shows an embodiment corresponding to FIG. 7, but wherein the connection branch 25 only extends radially of the annular portion 24. Even though the control unit 32 has been shown with larger dimensions than those of the connection branch 25, the control unit may, of course, be provided with outer dimensions being smaller to such an extent that the control unit, when mounting the control device on the elongate appliance, does not need an insertion opening which is larger than what corresponds to the outer dimensions of the connection branch 25.

FIG. 9 shows an embodiment in which the enclosure member includes two sections 20' and 20" acting oppositely on a common control unit 32. Accordingly, the two sections may be made of a flexible plastic material having a low elasticity coefficient so that, after a compression, the material is not able to return to its starting shape, as may be the case in the other embodiments. The working fluid 28 may be a fluid, paste or gel. When the enclosure section 20", shown to the right in FIG. 9 is compressed, as indicated at "P", a movable member in control unit 32 may be switched or displaced accordingly, and, moreover, the enclosure section 20', shown to the left, will be distended, because the control unit 32 may permit that working fluid 28 is transferred to section 20' or that the fluid 28 in section 20' is pressurized when compressing section 20", as shown. Thereafter, section 20' may be returned to its initial state by compressing section 20'. Accordingly, the embodiment of FIG. 9 will have at least two stable end positions. Although not shown in FIG. 9, the two annular portions 24' and 24" may be arranged coaxially relative to each other around an elongated appliance, with the control unit 32 in the interior of the appliance, and with the two connection branches 25', 25" extending through appropriate openings in the casing of the appliance.

Although the various connection branches 25 are shown extending radially from the respective annular enclosure portions 24, they may extend in other directions relative to the annular portion 24, e.g., by rolling or everting the same.

FIGS. 10–15 show various embodiments of the control unit 32. In FIGS. 10–12, the free end of branch portion 25 is closed by a movable wall in the shape of a bellows 30 which either has an inherent elasticity so that it tends to return to its starting position or is forced back by separate spring means. Alternatively, the bellows may be quite unresilient and forced back by a vacuum occurring in the interior of the branch portion 25, when the compressing or squeezing action on a resilient enclosure member ceases, whereby the enclosure member tends to return to its starting position. In FIG. 10, a connection rod 36 of unmagnetic material is attached to the movable end of the bellows, and the other end of the connection rod 36 carries a core 38 of magnetic or magnetizable material. When the bellows is moved, the connection rod 36 is displaced in its longitudinal direction, thereby providing corresponding changes in the magnetic field of a detector coil 40 having two terminals 26 for connection to a circuit including an actuatable device, such as a motor M, to be controlled, depending on the pressure in the enclosure and thereby on the degree of compression. The detector coil 40 may be seated around the end of the branch portion 25.

Also, FIG. 11 shows an embodiment including a bellows 30, but this one carries on its end face a capacitor plate 42 which is moved by the bellows to or from a second capacitor plate 44 which is stationarily secured relative to the enclosure branch portion 25 in a housing 46. Each capacitor plate is connected to a terminal 26. A similar arrangement is shown in FIG. 12, one capacitor plate being replaced by a sliding contact 52 which through a connection rod 45 is connected to the end face of the bellows, and the second capacitor plate being replaced by an electric resistance 54 and a slide bar 56, from which current may flow through the sliding contact 52 and to or from the resistance 54, with an amperage depending on the position of the sliding contact, which, in turn, depends on the position of the bellows 30 and the degree of compression of the enclosure member.

In FIG. 13 the enclosure branch portion 25 is closed by a membrane 48 to which a beam 50 of two layers of piezoelectric material is secured. When the membrane is moved by the pressure in the interior of the enclosure member, the beam is bent and its upper and lower faces are stretched or shortened, thus generating a voltage between the silver coatings on the upper and lower face of the beam. This voltage occurs across terminals 26 to which a circuit may be connected and thus powered or controlled in response to the degree of compression exerted on the enclosure, i.e., in response to the displacements of the working fluid 28.

In FIG. 14, the bellows or membrane is replaced by a piston 58, the movement thereof controlling or operating a micro switch 60 responsive to the compression of the enclosure member. In FIG. 15, the end of the enclosure branch portion 25 is closed by a flexible membrane 62 having a pressure plate 64 and a connection rod 66 which, depending on compression, pressure rise or displacement of working fluid 28, is moved to collapse a pressure medium containing tube piece 68, the ends thereof being closed and provided with contact electrodes 80. The interior of the tube piece 68 is filled up with an electrolyte or mercury, and when the tube piece 68 is completely collapsed, a current between the terminals 26 is interrupted. If the pressure medium is a conductive electrolyte, the amperage of a current between the electrodes 80 will decrease as a function of the degree of collapsing the tube piece 68.

I claim:

1. A hand-held appliance comprising a handle portion and at least one finger-operable control device for controlling a variably actuatable device associated with said appliance;
   said control device comprising a sealed and compressible enclosure member mounted on said handle portion, said enclosure member being filled with a working fluid;
   said enclosure member having a wall portion which is movable responsive to displacements in said working fluid upon squeezing said enclosure member against said handle portion, the movable wall portion being formed as part of a protruding tubular branch portion with a free end extending into the interior of said handle portion; and
   said movable wall portion being operatively connected with a movable member of a control unit in said handle portion, said control unit being arranged to variably control said actuatable device dependent on the extent of moving said movable member, whereby said actuatable device is variably actuated responsive to the degree of squeezing said enclosure member against said handle portion.

2. A hand-held appliance as defined in claim 1, wherein said movable wall portion is terminating and sealing the free end of said tubular branch portion.

3. A hand-held appliance as defined in claim 1, wherein said branch portion is terminated by a bellows, an end wall thereof constituting said movable wall portion.

4. A hand-held appliance as defined in claim 1, wherein said enclosure member comprises a generally annular hollow portion seated on said handle portion, the tubular branch portion protruding therefrom and into said handle portion, said movable wall portion terminating and sealing the free end of the branch portion.

5. A hand-held appliance as defined in claim 1, wherein said actuatable device comprises a motor.

6. A hand-held appliance as defined in claim 1, wherein said control unit comprises a detector coil, and wherein said movable member of the control unit comprises a core member, said core member being displaceable to change the magnetic field of the detector coil by squeezing said enclosure member and depending on the degree of said squeezing.

7. A hand-held appliance comprising a handle portion and at least one finger-operable control device for controlling a variably actuatable device associated with said appliance;
   said control device comprising a sealed and compressible enclosure member being filled with a working fluid;
   said enclosure member further comprising an exterior portion mounted on said handle portion and being squeezable thereagainst, and a branch portion protruding from said exterior portion and into the interior of said handle portion, said branch portion including a movable wall portion which is movable responsive to displacements in said working fluid upon squeezing said exterior enclosure member portion against said handle portion; and
   said movable wall portion being operatively connected with a movable core member adapted to change the magnetic field of a detector coil, whereby said actuatable device, when connected to terminals of said detector coil, is variably controlled responsive to the degree of squeezing said exterior enclosure member portion.

8. A hand-held device comprising a variably actuatable appliance; a relatively rigid handle portion connected to said appliance; means for variably actuating said appliance disposed in said handle portion; and a control device at least partially disposed on an exterior surface of said handle portion for controlling said means for actuating,
   said control device comprising:
   a sealed enclosure member filled with a working fluid and having a first portion disposed on the exterior surface of said handle portion in such manner that said portion is compressible against said handle portion by direct finger pressure, and
   said enclosure member having a second wall portion disposed within said handle portion, said wall portion being movable in response to displacement of said working fluid by finger pressure on said first portion, and
   said means for actuating including a movable member operatively associated with said second wall portion in such manner that the degree of compression of said first portion against said handle portion determines the variable actuation of said appliance.

9. An appliance according to claim 8 wherein said handle portion has a longitudinally-extending axis and wherein said first portion of said enclosure member extends parallel to the axis of said handle portion.

10. An appliance according to claim 8 wherein said first portion of said enclosure member defines a generally annular member surrounding said handle portion.

11. A hand-held appliance according to claim 1, wherein the variably actuatable device is moved from an operative condition to an inoperative condition by squeezing said enclosure member against said handle portion.

* * * * *